(12) United States Patent
Uematsu et al.

(10) Patent No.: US 7,943,347 B2
(45) Date of Patent: May 17, 2011

(54) NUCLEIC ACID AMPLIFICATION METHOD

(75) Inventors: Chihiro Uematsu, Kawasaki (JP); Yukie Nakashima, Shiki (JP); Toshiyuki Hatano, Hachioji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 243 days.

(21) Appl. No.: 12/155,189

(22) Filed: May 30, 2008

(65) Prior Publication Data

US 2008/0318282 A1    Dec. 25, 2008

(30) Foreign Application Priority Data

Jun. 21, 2007 (JP) .................................. 2007-163601

(51) Int. Cl.
*C12P 19/34* (2006.01)
*C12Q 1/68* (2006.01)

(52) U.S. Cl. .................. 435/91.2; 435/91.21; 435/6

(58) Field of Classification Search ............. 435/6, 91.2, 435/91.21
See application file for complete search history.

(56) References Cited

U.S. PATENT DOCUMENTS

| | | |
|---|---|---|
| 6,410,278 B1 | 6/2002 | Notomi et al. |
| 2007/0212695 A1 * | 9/2007 | Aivazachvili et al. ............ 435/6 |

FOREIGN PATENT DOCUMENTS

| | | |
|---|---|---|
| WO | WO87/06270 | 4/1987 |
| WO | WO 91/01384 | 7/1990 |

OTHER PUBLICATIONS

Wang, Alice M. et al., "Quantitation of mRNA by the polymerase chain reaction", Proc. Natl. Acad. Sci. USA, vol. 86, pp. 9717-9721, Dec. 1989.
Edwards, K. et al., Book Review, JAC, the British Society for Antimicrobial Chemotherapy, vol. 54 No. 5, p. 968, 2004.
Saiki, Randall K., "Primer-Directed Enzymatic Amplification of DNA with Thermostable DNA Polymerase", Science, Reports, pp. 487-491, Jan. 29, 1988.
Compton, J., "Nucleic acid sequence-based amplification", Nature, vol. 350, pp. 91-92, Mar. 7, 1991.
Walker, G. Terrance et al., "Isothermal in vitro amplification of DNA by a restriction enzyme/ DNA polymerase system", Proc. Natl. Acad. Sci. USA, vol. 89, pp. 392-396, Jan. 1992.
Guatelli, John C. et al., "Isothermal, in vitro amplification of nucleic acids by a multienzyme reaction modeled after retroviral replication", Pro. Natl. Acad.Sci., vol. 87, pp. 1874-1978, Mar. 1990.
Notomi, Tsugunori, et al., "Loop-mediated isothermal amplification of DNA", Nucleic Acids Research, vol. 28 No. 12, 2002.

\* cited by examiner

*Primary Examiner* — Gary Benzion
*Assistant Examiner* — Cynthia B Wilder
(74) *Attorney, Agent, or Firm* — Stites & Harbison PLLC; Juan Carlos A. Marquez, Esq.

(57) ABSTRACT

Provided is a simple and highly sensitive nucleic acid amplification method including hybridizing two types of oligonucleotide probes with a target gene and ligating the oligonucleotide probes with DNA ligase and amplifying the resultant single-stranded oligonucleotide in accordance with LAMP.

8 Claims, 9 Drawing Sheets

NUCLEIC ACID AMPLIFICATION METHOD

CLAIM OF PRIORITY

The present application claims priority from Japanese application JP 2007-163601 filed on Jun. 21, 2007, the content of which is hereby incorporated by reference into this application.

BACKGROUND OF THE INVENTION

1. Field of the Invention

The present invention relates to a method for amplifying a nucleic acid (DNA or RNA), and more particularly, to an isothermal nucleic acid amplification method performed in combination with the LAMP method using a heat resistant ligase and DNA polymerase having strand displacement activity.

2. Background Art

In the life phenomenon research, amplification of DNA and RNA has been used for various purposes. As examples of a method for gene expression analysis and a method for qualification of gene expression level, a competitive PCR method (A. Wang, et al., Proc Natl Acad Sci USA, 86, 9717-9721(1989) and a real-time PCR method (K. Edwards, et al., Journal of Antimicrobial, 54, 968 (2004) etc. are known. They each employ a general nucleic acid amplification method, PCR (polymerase chain reaction) method (R. K. Saiki, et al., Science, 239, 487-491 (1988)) to determine the expression level of a gene based on the amplified gene.

The nucleic acid amplification method for use in the aforementioned analyses is constituted of three steps: denaturing double stranded DNA into a single stranded DNA, annealing to hybridize a primer with the single stranded DNA, elongating the primer to form a complementary chain, or constituted of two steps: denaturation and elongation. In both cases, a cycle consisting of a high temperature step and a low temperature step is inevitably performed repeatedly. This cycle of the PCR method must be performed by use of a thermal cycler capable of accurately controlling temperature. Furthermore, the time required for adjusting the temperature of an apparatus and a reaction solution to a predetermined value increases as the number of cycles increases. Consequently, it takes long time for analysis.

Then, to overcome the aforementioned problems, a method has been developed for amplifying a nucleic acid at isothermal conditions. As examples of such an isothermal nucleic acid amplification method, the following are principally known:

NASBA (Nucleic Acid Sequence-Based Amplification) method (J. Compton, et. al., Nature, 350, 91-92 (1991);

SDA (strand displacement amplification) method (G. T. Walker, et. al., Proc. Natl. Acad. Sci USA, 89, 392-396 (1992));

3SR (self-sustained sequence replication) method (J. C. Guatelli, et al., Proc Natl Acad Sci USA, 87, 1874-1878 (1990));

TMA (transcription-mediated amplification) method (JP Patent No. 3241717);

QB replicase amplification method (JP Patent No. 2710159); and

LAMP (loop-mediated isothermal amplification) method (JP Patent No. 3313358 and T. Notomi, et al., Nucleic Acids Research, 28, e63 (2000)).

In these isothermal nucleic acid amplification methods, elongation of a primer, annealing of the primer to hybridize with a single stranded elongation product, and the following elongation of the primer are performed in a reaction mixture maintained at a constant temperature.

Of these isothermal nucleic acid amplification methods, an SDA method and a LAMP method employ DNA polymerase having strand displacement activity. In the SDA method, dATPαS is used as a substrate in place of dATP to provide a priming site serving as an amplification initiation point. In the LAMP method, a primer elongation product is designed to form a self-looped structure. The SDA method has a problem in that an efficiency of an enzyme for incorporating a substrate is low, decreasing amplification efficiency. The LAMP method has a problem in that it is difficult to design a primer. More specifically, it is difficult to design optimal primers in accordance with various detection items. In the circumstances, it has been desired to develop an isothermal nucleic acid amplification method to overcome these problems.

SUMMARY OF THE INVENTION

A primary object of the present invention is to provide a method capable of detecting expression of a gene or quantifying the expression level of the gene simply and with high sensitivity by overcoming problems associated with conventional isothermal nucleic acid amplification methods.

To overcome the aforementioned problems, the present inventors found an isothermal nucleic acid amplification method by introducing common sequences into a template nucleic acid by use of DNA ligase, and amplifying the nucleic acid by using DNA polymerase having strand displacement activity.

The present invention employs two types of oligonucleotide probes each having a base sequence that recognizes a target gene and a base sequence irrelevant to the target gene. The two types of oligonucleotide probes are each allowed to recognize the target gene and hybridize with it, and then, these two types of oligonucleotide probes are ligated with DNA ligase. One of the oligonucleotide probes to be ligated has a base sequence recognizing the target gene at the 5' end side and a base sequence irrelevant to the target gene at the 3' end side. The 5' end of this oligonucleotide probe is phosphorylated. The other oligonucleotide probe has a base sequence irrelevant to the target gene at the 5' end side and a base sequence recognizing the target gene at the 3' end side.

When a target gene is present, two types of oligonucleotide probes hybridize with the target gene at the 5' end side and the 3' end side, respectively, and ligated with DNA ligase. Conversely, when a target gene is not present, two types of oligonucleotide probes are not ligated with each other and the following reaction will not occur.

The ligated oligonucleotide probe has base sequences irrelevant to the target gene at the 5' end and the 3' end. LAMP primers are designed so as to meet an identical sequence or complementary sequence to the irrelevant base sequences to the target gene. Thereafter, isothermal amplification is performed using DNA polymerase having strand displacement activity. The sequence from which amplification is initiated can be designed independently of the target gene, and needs not be changed even if a different gene is targeted. The sequence from which amplification is initiated can be used universally. In addition, if the portions of two types of oligonucleotide probes to be hybridized with a target gene are only changed (to prepare a plurality of oligonucleotide probe sets), a plurality of target genes can be detected at the same time. In short, multiplex amplification can be performed. Since the primers involved in amplification can be used in common, a plurality of oligonucleotide probe sets may be used in combination with the common amplification primer.

More specifically, the present invention relates to a method for amplifying a nucleic acid including:

a step of hybridizing a 1st probe, which has a 1st sequence complementary to a target nucleic acid at the 3' end and a 2nd sequence noncomplementary to the target nucleic acid at the 5' end, and a 2nd probe, which has a 3rd sequence noncomplementary to the target nucleic acid at the 3' end and a 4th sequence complementary to the target nucleic acid at the 5' end which is phosphorylated, with the target nucleic acid;

a step of forming a template by ligating the 3' end of the 1st probe hybridized with the target nucleic acid to the 5' end of the 2nd probe hybridized with the target nucleic acid by a ligation reaction; and a step of amplifying the template by repeating the following steps (1) to (7):

(1) a step of hybridizing a 1st primer, which has a 5th sequence noncomplementary to the 3rd sequence at the 5' end and a 6th sequence complementary to a part of the 3rd sequence at the 3' end, with the template, and elongating the 1st primer, thereby obtaining a 1st amplification template;

(2) a step of hybridizing a 2nd primer, which has a 7th sequence complementary to a region of the 3rd sequence, which is closer to the 3' end than the region complementary to the 6th sequence, and elongating the 2nd primer with DNA polymerase having strand displacement activity, thereby dissociating the 1st amplification template from the aforementioned template;

(3) a step of hybridizing a 3rd primer, which has an 8th sequence noncomplementary to the complementary sequence to the 2nd sequence at the 5' end and a 9th sequence containing a part of the 2nd sequence at the 3' end, with the 1st amplification template dissociated, and elongating the 3rd primer, thereby obtaining a 2nd amplification template;

(4) a step of hybridizing a 4th primer, which has a 10th sequence complementary to a region of the 2nd sequence, which is closer to the 5' end than the sequence complementary to the 9th sequence, with the 1st amplification template dissociated, and elongating the 4th primer by DNA polymerase having strand displacement activity; thereby dissociating the 2nd amplification template from the 1st amplification template:

(5) a step of synthesizing a complementary chain from the 3' end of the 2nd amplification template;

(6) a step of hybridizing a 5th primer, which has at least a part of the 5th sequence at the 5' end and at least a part of the 6th sequence at the 3' end, with a loop formed at the 3' end side of the 2nd amplification template, elongating the 5th primer by use of DNA polymerase having strand displacement activity to displace the complementary chain synthesized in the step (5), thereby rendering the 3' end of the chain displaced to be capable of forming base pairing; and (7) a step of using the chain whose 3' end is rendered to be capable of forming base pairing in the step (6) as a new template to be used in the step (5).

The method may further include the following steps:

(8) a step of synthesizing a complementary chain from the 3' end of the new template;

(9) a step of hybridizing a 6th primer, which has at least a part of the 8th sequence at the 5' end and at least a part of the 9th sequence at the 3' end, with a loop to be formed at the 3' end side of the new template, elongating the 6th primer with DNA polymerase having strand displacement activity to displace the complementary chain synthesized in the step (8), thereby rendering the 3' end of the chain displaced to be capable of binding to a base; and

(10) a step of using the chain whose 3' end is rendered to be capable of binding to a base in the step (9) as the new template to be used in the step (5).

It is preferable but not inevitable that the 5th primer is identical with the 1st primer and that the 6th primer is identical with the 3rd primer.

In the LAMP method, in addition to the aforementioned 1st to 4th primers, use can be made of a loop primer, which hybridizes with a loop formed at the 5' end side of the amplification template. Examples of such a loop primer include a 7th primer, which is capable of hybridizing with a loop formed at the 5' end side of the 2nd amplification template and has a sequence complementary to at least a part of the 8th sequence; and an 8th primer, which is capable of hybridizing with a loop formed at the 5' end side of the new template and has a sequence complementary to at least a part of the 5th sequence. Use of these primers enables all loops on the template to be involved in amplification, increasing amplification efficiency.

To prevent a false positive reaction, the 3' end of the 3rd sequence of the 2nd probe is desirably modified with phosphorylation or amination.

In the method of the present invention, a plurality of types of target nucleic acids can be simultaneously amplified and detected in a single reaction tube by hybridizing two types of oligonucleotide probes as mentioned above with each of the target nucleic acids, ligating them by a ligation reaction, and allowing the 1st, 2nd, 3rd and 4th primers to act on each of the ligated oligonucleotide probes.

In the present invention, there is provided a kit for a nucleic acid amplification method according to the present invention. The kit of the present invention essentially include a 1st probe having a 1st sequence complementary to a target nucleic acid at the 3' end and a 2nd sequence noncomplementary to the target nucleic acid at the 5' end;

a 2nd probe having a 3rd sequence noncomplementary to the target nucleic acid at the 3' end and a 4th sequence complementary to the target nucleic acid at the 5' end, which is phosphorylated;

a 1st primer having a 5th sequence noncomplementary to the 3rd sequence at the 5' end and a 6th sequence complementary to a part of the 3rd sequence at the 3' end;

a 2nd primer having a 7th sequence complementary to a region of the 3rd sequence, which is closer to the 3' end than the region complementary to the 6th sequence;

a 3rd primer having an 8th sequence noncomplementary to the complementary sequence to the 2nd sequence at the 5' end and a 9th sequence containing a part of the 2nd sequence at the 3' end; and a 4th primer having a 10th sequence containing a part of the 2nd sequence, which is closer to the 5' end than the sequence containing a part of the 9th sequence.

The kit may contain a 7th primer having a complementary sequence to at least a part of the 8th sequence, and further include a 8th primer having a complementary sequence to at least a part of the 5th sequence.

The kit may include not only the primers but also various types of reaction solutions such as a strand displacement DNA polymerase and ligase, other constitutional elements required for carrying out the amplification method of the present invention.

As described above, to prevent a false positive reaction, the 3' end of the 3rd sequence of the second probe is desirably modified by phosphorylation or amination.

In the present invention, two types of oligonucleotide probes are hybridized with a target gene and ligated with DNA ligase. The resultant single stranded oligonucleotide probe is subjected to LAMP amplification. By virtue of this, LAMP amplification primers, which are difficult to design by conventional method, can be designed no matter which sequence a target gene has. In addition, the primers and detection probes can be used universally. Furthermore, a plurality of targets can be simultaneously amplified simply by the LAMP reaction, although such a multiplex reaction is difficult to attain by conventional methods. Moreover, in the present invention, the presence or absence of a target nucleic acid can be determined based on ligation of two types of oligonucleotide probes. Since detection of the ligated oligonucleotide probe is performed by the LAMP method, detection can be attained with higher sensitivity. In short, a simple and highly sensitive nucleic acid amplification method can be realized by the present invention.

Figure 1:
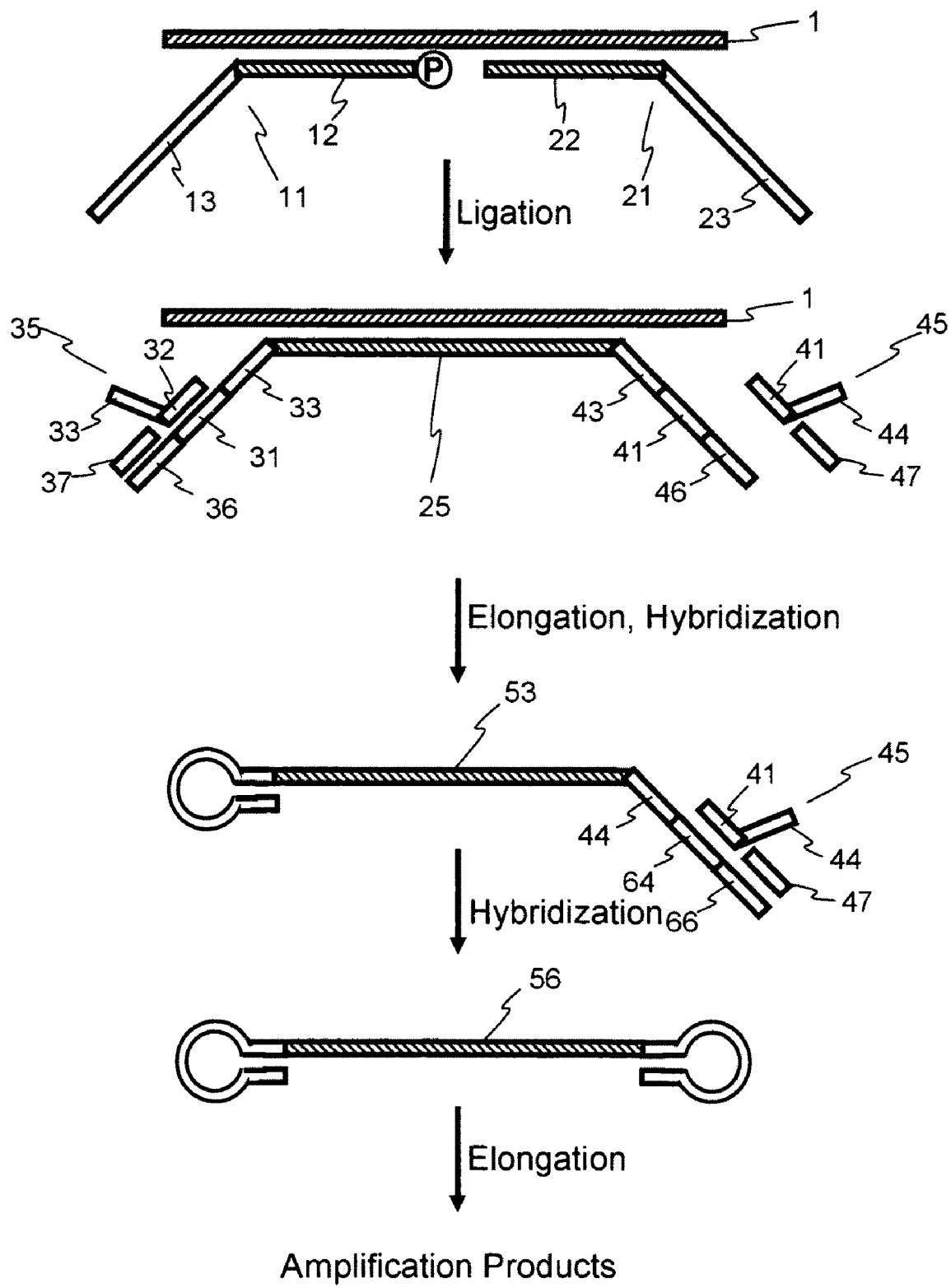
FIG. 1 is an illustration showing a first flow of the present invention.

DESCRIPTION OF SYMBOLS 1, 131, 141, 151 . . . Target gene
11, 106, 132, 142, 152 . . . Phosphorylated oligonucleotide probe
12, 22 . . . Base sequence specific to target gene
13, 23 . . . Base sequence irrelevant to target gene
21, 107, 133, 143, 153 . . . Oligonucleotide probe
25, 108, 135, 145, 155 . . . Ligated oligonucleotide probe
31, 32, 33, 36, 41, 43, 44, 46, 64, 66 . . . Base sequence
35, 37, 45, 47, 102, 111, 112, 121, 122, 161, 162, 163, 164 . . . Primer
51, 52, 54, 55 . . . Single-stranded DNA
53 . . . DNA having a loop structure
56 . . . DNA having a dumbbell structure
61, 62, 71, 72 . . . Double-stranded DNA
81, 82, 83, 85, 86, 87, 88 . . . DNA structure
84, 116 . . . DNA having a dumbbell structure
101 . . . Target RNA
105 . . . cDNA
115 . . . Elongation product
171 . . . Electrophoresis gel image
181 . . . Graph showing real-time detection results of amplified products

DETAILED DESCRIPTION OF THE PREFERRED EMBODIMENTS

The first flow of the present invention is shown in FIG. 1. The present invention, which is directed to a method for amplifying and detecting a nucleic acid sequence, employs an oligonucleotide probe 11,
which has a base sequence 12 having a sequence specific to a base sequence of a target gene 1, and a base sequence 13 having a sequence irrelevant to the base sequence of the target gene 1, and which has a phosphorylated 5' end;

an oligonucleotide probe 21,
which has a base sequence 22 having a sequence specific to a base sequence of the target gene 1, and a base sequence 23 having a sequence irrelevant to the base sequence of the target gene 1;

a primer 35,
which has a base sequence 32 complementary to a base sequence 31, which is a part of the base sequence 13 irrelevant to the base sequence of the target gene 1, on the 3' end side, and has a base sequence identical with a base sequence 33, which is a part of the base sequence 13 positioned closer to the 5' end than the base sequence 31;

a primer 37,
which has a base sequence complementary to a base sequence 36, which is a part of the base sequence 13 positioned closer to the 3' end side than the base sequence 31;

a primer 45,
which has a sequence identical with a base sequence 41, which is a part of the base sequence 23 irrelevant to the base sequence of the target gene 1, at the 3' end side, and has a base sequence 44 complementary to a base sequence 43, which is a part of the base sequence 23 positioned closer to the 3' end side than the base sequence 41, at the 5' end side; and a primer 47,
which has a base sequence identical with a base sequence 46, which is a part of the base sequence 23 positioned closer to the 5' end side than the base sequence 41.

The method of the present invention is characterized by having a first step of hybridizing the oligonucleotide probe 11 and oligonucleotide probe 21 with the target gene 1, and ligating the oligonucleotide probe 11 and the oligonucleotide probe 21 by a ligation reaction; and a second step of allowing the primer 35, primer 37, primer 45 and primer 47 to act on the ligated oligonucleotide probe 25 obtained in the first step and amplifying a double stranded DNA.

Examples of the ligase for use in ligation may include Pfu DNA ligase, Taq DNA ligase, T4 DNA ligase and *E-coli* DNA ligase.

In the second step, an amplified product is obtained by substantially performing the LAMP reaction using the ligated oligonucleotide probe 25 as a template. Accordingly, the DNA polymerase to be used in the present invention is DNA polymerase having strand displacement activity. Examples of the DNA polymerase having strand displacement activity may include Bst DNA polymerase, phi29 DNA polymerase, Klenow Fragment, Klenow Fragment (3'→5' exo), Vent DNA polymerase, Vent (exo-) DNA polymerase, Deep Vent DNA polymerase, Deep Vent (exo-) DNA polymerase, 9 Nm DNA polymerase and Therminator DNA polymerase. In the second step, the primer 35 and the primer 37 are allowed to act on the ligated oligonucleotide probe 25 (single stranded DNA) to obtain DNA 53 having a loop structure. Thereafter, the primer 45 and the primer 47 are allowed to act on the DNA 53 having a loop structure to obtain DNA 56 having a dumbbell structure serving as an amplification initiation point in the LAMP reaction. Finally, amplification products are obtained.

Figure 2:
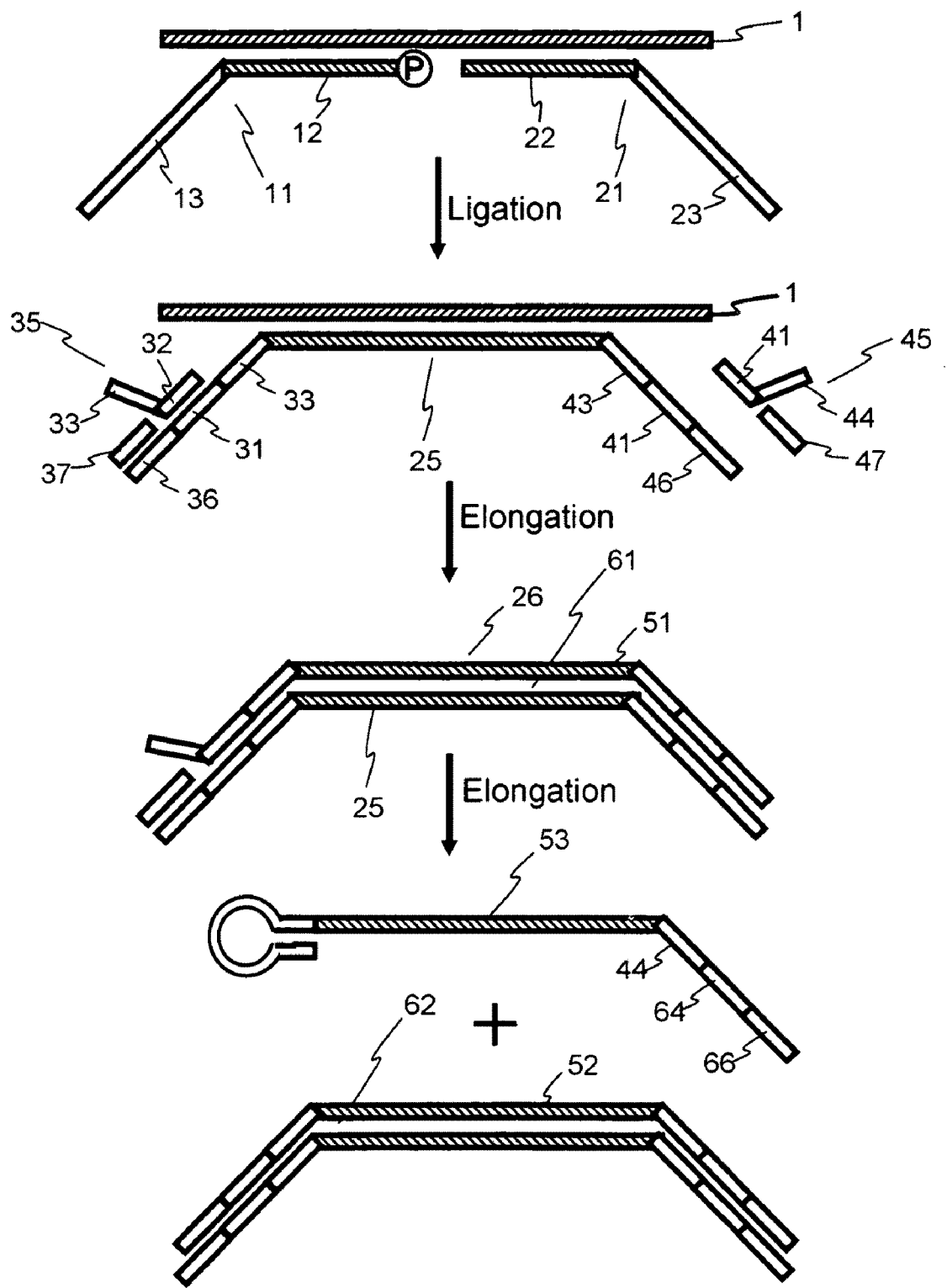
FIG. 2 is an illustration showing a process of the first flow of the present invention until DNA having a dumbbell structure, which serves as an initiation point of amplification, is obtained.
Figure 2:
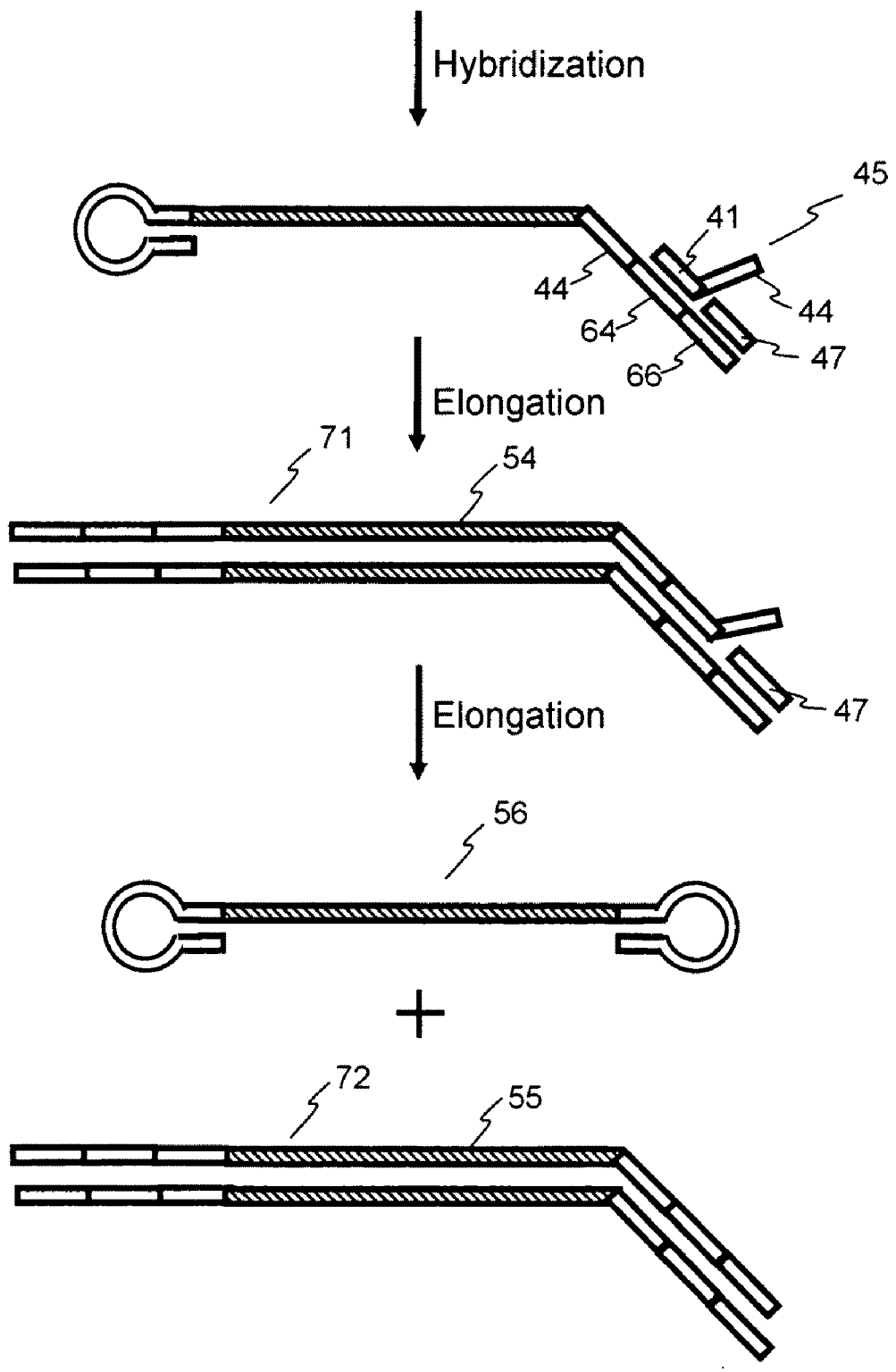

Of the first flow, the process until DNA 56 having a dumbbell structure serving as an amplification initiation point is obtained, is more specifically shown in FIG. 2.

The oligonucleotide probe 11 (which has a base sequence 12 having a sequence specific to a base sequence of a target gene 1, and a base sequence 13 having a sequence irrelevant to the base sequence of the target gene 1, and which has a phosphorylated 5' end), and the oligonucleotide probe 21 (which has the base sequence 22 having a sequence specific to a base sequence of the target gene 1, and the base sequence 23 having a sequence irrelevant to the base sequence of the target gene 1) are hybridized with the target gene 1. Then, a ligation reaction is performed to ligate the oligonucleotide probe 11 (having a phosphorylated 5' end) and the oligonucleotide probe 21. In this manner, the ligated oligonucleotide probe 25 is obtained.

Next, the primer 35 (which has a base sequence 32 complementary to a base sequence 31, which is a part of the base sequence 13 irrelevant to the base sequence of the target gene 1, on the 3' end side, and has a base sequence identical with a base sequence 33, which is a part of the base sequence 13 positioned closer to the 5' end than the base sequence) and the primer 37 (which has a base sequence complementary to a base sequence 36, which is a part of the base sequence 13 positioned closer to the 3' end side than the base sequence 31) are hybridized with the obtained single stranded DNA, i.e., the ligated oligonucleotide probe 25, and elongated. First, the primer 35 elongates along the ligated oligonucleotide probe 25 serving as a template, leading to a single stranded DNA 51. Since the single stranded DNA 51 and the ligated oligonucleotide probe 25 are hybridized, a double stranded DNA 61 is virtually obtained. Subsequently, the primer 37 elongates while dissociating the single stranded DNA 51 from the double stranded DNA 61, leading to a single stranded DNA 52. Since the single stranded DNA 52 and the ligated oligonucleotide probe 25 are hybridized, a double stranded DNA 62 is virtually obtained. The single stranded DNA 51 dissociated from the ligated oligonucleotide probe 25 has the base sequence 33 at the 5' end and the complementary sequence to the base sequence 33 (which is contained in the ligated oligonucleotide probe 25 serving as the template). The base sequence 33 and the complementary sequence thereof are hybridized with each other in the same molecule, leading to a DNA 53 having a loop structure at the 5' end.

The DNA 53 having a loop structure has complementary sequences to the base sequences 41, 43 and 46 contained in ligated oligonucleotide probe 25 as a template; more specifically, has a base sequence 66 complementary to the base sequence 46 at the 3' end side, a base sequence 64 complementary to the base sequence 41 at a position closer to the 5' end side than the base sequence 66, and a base sequence 44 complementary to the base sequence 43 at a position closer to the 5' end than the base sequence 64. Then, the primer 45 (which has the base sequence 41 at the 3' end side and the base sequence 44 at the 5' end side) and the primer 47 are hybridized with DNA 53 having a loop structure and elongated. First, the primer 45 elongates along with DNA 53 having a loop structure serving as a template, leading to a single stranded DNA 54. The single stranded DNA 54 elongates while unwinding the loop structure of the DNA 53 to form a hybrid, a double stranded DNA 71. Subsequently, the primer 47 elongates while dissociating the single stranded DNA 54 from the double stranded DNA 71, leading to a single stranded DNA 55. The single stranded DNA 55 also forms a hybrid while dissociating the single stranded DNA 54, leading to a double stranded DNA 72. The single stranded DNA 54 dissociated has the base sequence 44 at the 5' end and the base sequence 43, which is complementary to the base sequence 44 of the single stranded DNA 53 serving as a template. Therefore, the base sequences 44 and 43 are hybridized with each other in the same molecule to form a loop structure at the 5' end. In addition, since the single stranded DNA 54 is synthesized with DNA 53 having a loop structure used as a template, DNA 54 has a sequence complementary to the base sequence 33 at the 3' end and the base sequence 33 within the molecule. Therefore, a loop structure is formed also at the 3' end. As a result, DNA 54 has a loop structure at both ends (5' end and 3' end), leading to DNA 56 having a dumbbell structure. Amplification according to the LAMP reaction starts from the DNA 56 having a dumbbell structure.

Figure 3:
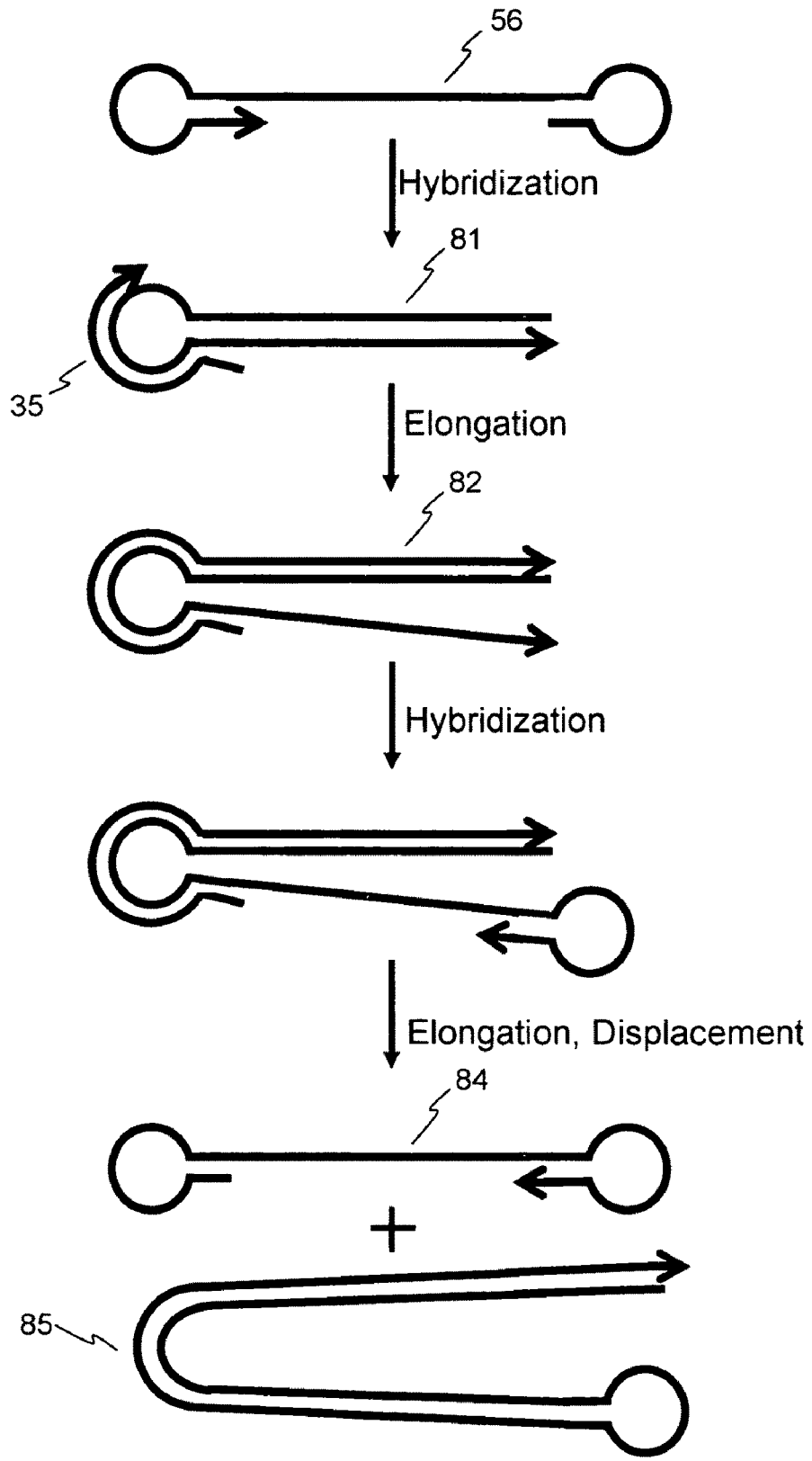
FIG. 3 is an illustration showing that DNA having a dumbbell structure serves as an amplification initiation point.
Figure 3:
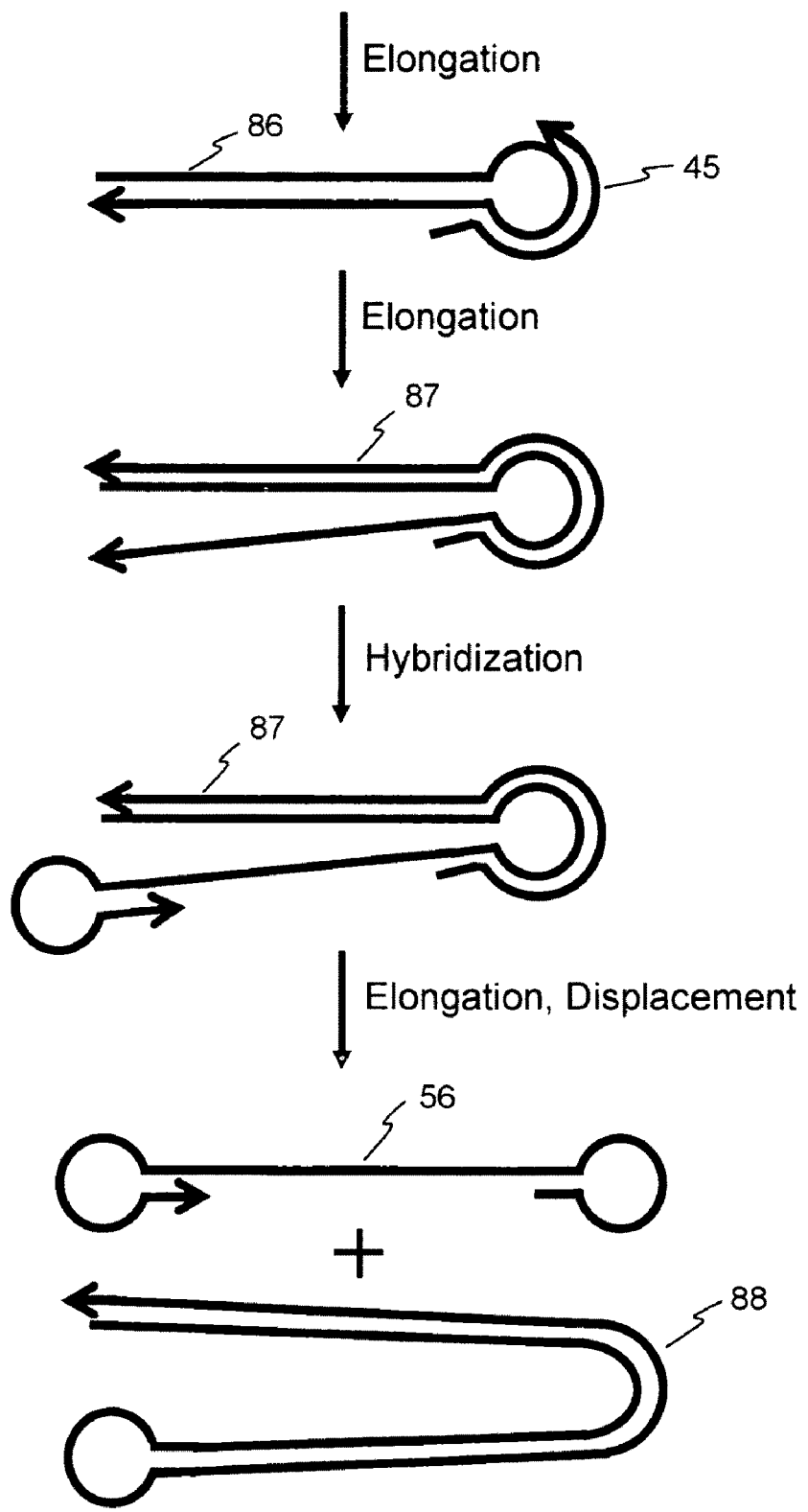

Amplification in accordance with the LAMP reaction starting from DNA 56 having a dumbbell structure is shown in FIG. 3. The details thereof should be referred to the publication of T. Notomi, et al. (Nucleic Acids Research, 28, e63 (2000)). Since DNA 56 having a dumbbell structure has a loop structure at the 3' end, it elongates to form a DNA structure 81, with the primer 35 hybridized at the loop structure at the 3' end. The primer 35 hybridized with the DNA structure 81 elongates while dissociating the double strand by DNA polymerase having strand displacement activity, leading to a DNA structure 82.

The DNA structure 82 has a loop structure at the 3' end. A chain elongates from the 3' end portion while dissociating the chain elongated from the primer 35, leading to a DNA structure 85. The dissociated chain elongated from the primer 35 is complementary to the DNA 56, leading to DNA 84 having a dumbbell structure.

From the DNA 84 having a dumbbell structure, DNA 56 having a dumbbell structure is regenerated in the same process as described above. To explain more specifically, DNA 84 elongates by itself from the 3' end having a loop structure; at the same time, the primer 45 is hybridized with the loop structure, leading to a DNA structure 86. The primer 45 hybridized with the DNA structure 86 elongates while dissociating the double strand with DNA polymerase having strand displacement activity, leading to a DNA structure 87.

The DNA structure 87 has a loop structure at the 3' end. Therefore, the DNA structure 87 elongates by itself from the 3' end portion, while dissociating the chain elongating from the primer 45, leading to a DNA structure 88. The dissociated elongation chain from the primer 45 is complementary to DNA 84, in other words, identical with DNA 56. This is used as a new template and the amplification reaction further proceeds.

In the aforementioned amplification step, the loop portion at the 3' end side having a dumbbell structure alone is involved in the amplification reaction. If a primer (loop primer of the LAMP method) complementary to the loop at the 5' end side is also used, all loops can be used for the amplification reaction, improving amplification efficiency. Such a loop primer can be used also in the present invention.

As described above, according to the present invention, oligonucleotide probes are ligated or not in accordance with the presence or absence of a target gene. Primers are designed so as to correspond to a portion irrelevant to a target gene sequence of the ligated oligonucleotide probe. Using the primers and the ligated oligonucleotide probe as a template, a LAMP reaction is performed. More specifically, a primer is designed such that it has a sequence complementary to a part of a sequence of the template which is irrelevant to a target gene sequence, at the 3' end and, at the 5' end portion, it has a sequence identical with a sequence of the template, which is present in the elongation direction of the sequence complementary to the aforementioned 3' end portion of the primer. Another primer is designed such that it hybridizes with a portion of the template at a position closer to the 3' end than the position at which the aforementioned primer is hybridized, such that the elongation product from the aforementioned primer can be dissociated with DNA polymerase having strand displacement activity. The aforementioned two primers are placed at the forward side and reverse side, respectively. Then, the LAMP reaction is performed. In conventional methods for the LAMP reaction, it was difficult to design primers. To describe more specifically, trial and error must be repeated to obtain a primer set which never cause a false positive reaction. However, in the present invention, primers are designed so as to correspond to the region irrelevant to a target gene sequence. Therefore, even if a different gene is targeted, it is only necessary to replace just the portions of the oligonucleotide probes complementary to a target gene sequence. The primer sets can be used universally. The system of the LAMP reaction can be easily set without a trial-and-error process for primer design.

Figure 4:
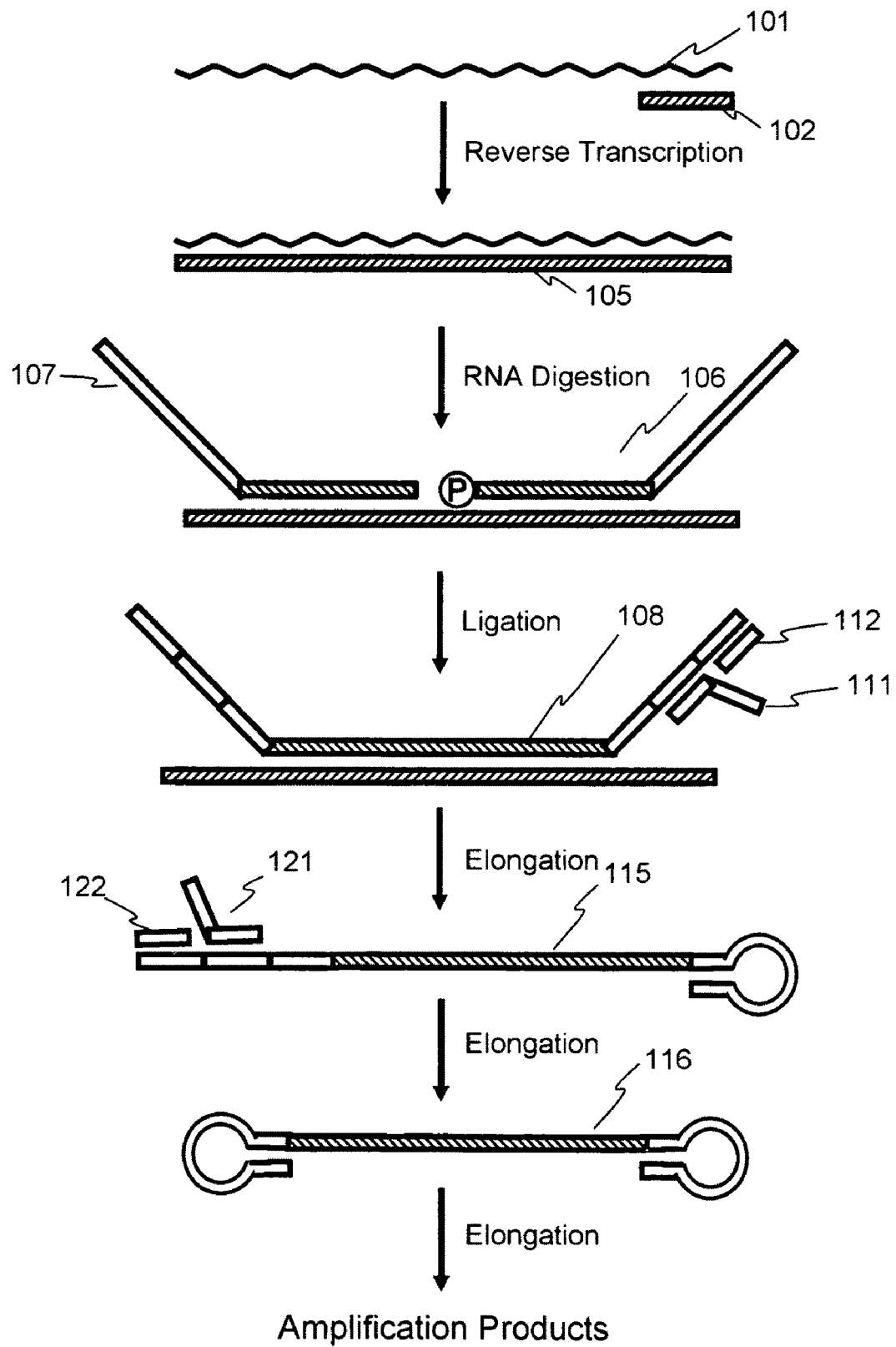
FIG. 4 is an illustration showing a second flow of the present invention.

The second flow of the present invention is shown in FIG. 4. In this method, reverse transcription is performed using a primer 102 having a specific sequence to a target RNA 101. After the reverse transcription, RNase treatment is performed to obtain cDNA 105. An oligonucleotide probe 106 is prepared so as to have a specific sequence to the cDNA 105 at the 5' end side and an irrelevant sequence to the cDNA 105 at the 3' end side. The 5' end of the probe 106 is phosphorylated. An oligonucleotide probe 107 is prepared so as to have an irrelevant sequence to the cDNA 105 at the 5' end side and a specific sequence to the cDNA 105 at the 3' end. The oligonucleotide probes 106 and 107 are hybridized with cDNA 105. Thereafter, the oligonucleotide probe 106 and the oligonucleotide probe 107 are ligated by a ligation reaction to obtain a ligated oligonucleotide probe 108.

The following process is performed in the same manner as shown in the first flow. More specifically, primers are designed so as to correspond to the portion of the ligated oligonucleotide probe 108 irrelevant to the target gene sequence. Using the primers, the LAMP reaction is performed using the ligated oligonucleotide probe 108 as a template. To explain more specifically, first, forward primers 111 and 112 are designed so as to correspond to the portion of the ligated oligonucleotide probe 108 irrelevant to the target gene sequence. The forward primers 111 and 112 are hybridized with the ligated oligonucleotide probe 108 and elongated with DNA polymerase having strand displacement activity. The forward primer 111 is designed so as to have a sequence hybridizing with the sequence of the oligonucleotide probe 106 irrelevant to the target gene sequence, at the 3' end and so as to have a sequence complementary to the sequence that will be synthesized when the 3' end is elongated, at the 5' end (in other words, the primer 111 is designed so as to have, at the 5' end, a sequence identical with a partial sequence of the template oligonucleotide probe 106, which is irrelevant to the sequence of the target gene sequence and will serve as a template when the 3' end of the primer 111 elongates). The primer 112 is designed so as to hybridize upstream of the hybridization position of the primer 111 such that the elongation product of the primer 111 can be dissociated by the elongation reaction of DNA polymerase having strand displacement activity. The elongation product 115 of the primer 111 is dissociated by elongation of the primer 112 from the template and forms a loop structure at the 5' end.

With the elongation product 115 of the primer 111, a primer 121 and a primer 122 are hybridized. The primers are elongated by use of DNA polymerase having strand displacement activity. The primer 121 is designed so as to have a sequence, which can hybridize with a complementary sequence to the sequence of the oligonucleotide probe 107 irrelevant to the target gene sequence, at the 3' end. The primer 121 is also designed so as to have a complementary sequence to the sequence that will be synthesized when the 3' end elongates (in other words, the primer 121 is designed so as to have, at the 5' end, a sequence identical with a partial sequence of the elongation product 115, which is irrelevant to the sequence of the target gene sequence and will serve as a template when the 3' end of the primer 121 elongates). The primer 122 is designed so as to hybridize upstream of the hybridization position of the primer 121 such that the elongation product of the primer 121 can be dissociated by the elongation reaction of the DNA polymerase having strand displacement activity. The elongation product 116 of the primer 121 is dissociated from the template by the primer 122, leading to DNA 116 having a dumbbell structure having a loop structure at both ends (5' end and 3' end). Amplification is initiated from DNA 116 having a dumbbell structure in accordance with the LAMP reaction. More specifically, a ligation product is produced by ligating two types of oligonucleotide probes if a target RNA is present. A LAMP reaction is applied to the ligation product by using a set of primers, which hybridize with sequences irrelevant to the base sequence of the target RNA. Based on the presence or absence of amplified products, the presence or absence of the target RNA can be determined. When another type of RNA is used as a target, the presence or absence of the RNA can be determined in the same manner except that the reverse transcription primer and only the sequence portions of two types of oligonucleotide probes specific to the target RNA base sequence are changed. Primers for the LAMP reaction can be designed without a trial-and-error process. A primer set universally used can be provided.

Figure 5:
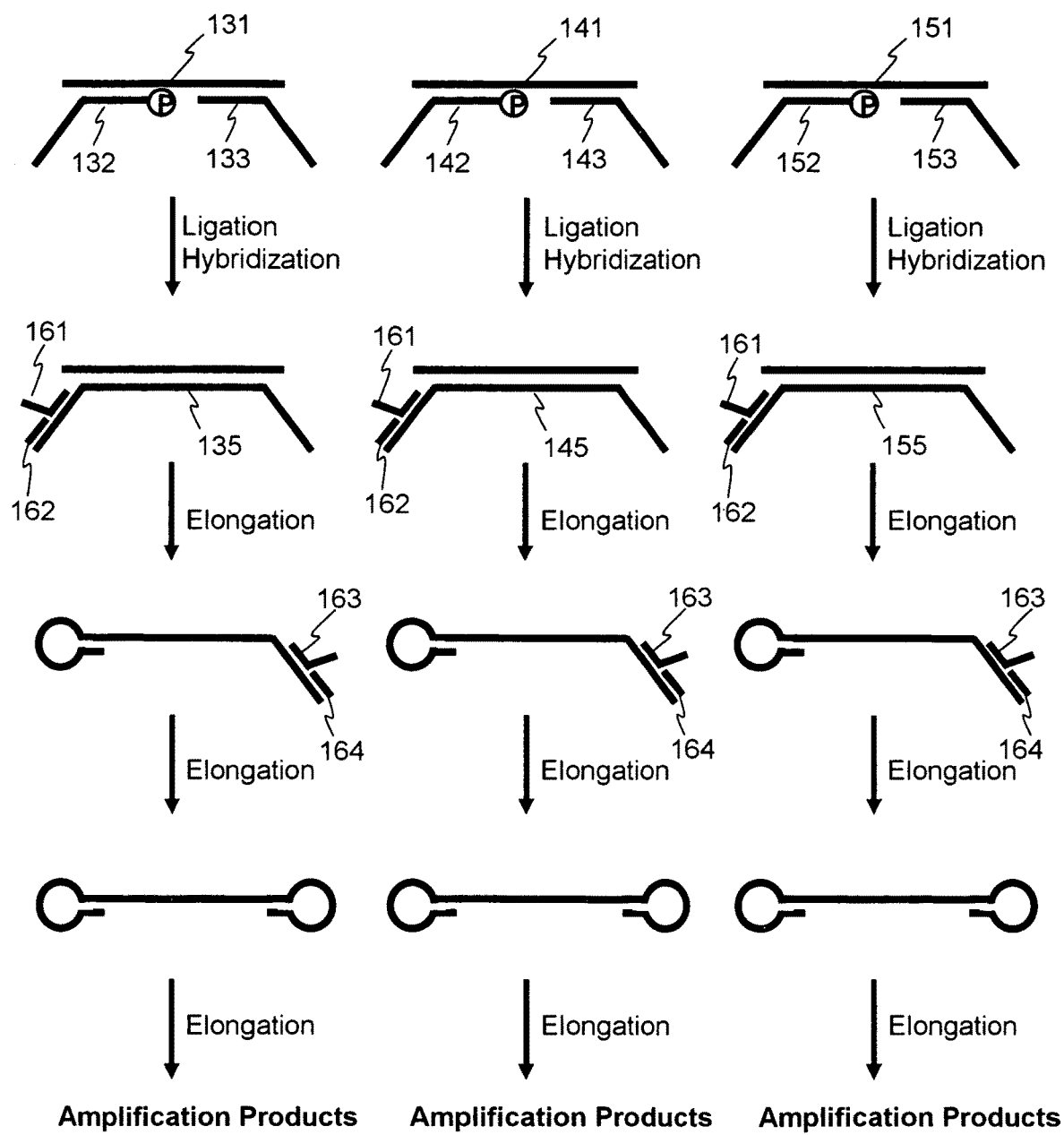
FIG. 5 is an illustration showing a third flow of the present invention.

The third flow of the present invention is shown in FIG. 5. To a plurality of target genes 131, 141 and 151, pairs of oligonucleotides 132/133, 142/143 and 152/153 are hybridized respectively. The oligonucleotide probes 132, 142 and 152 each have a specific sequence to the target gene, at the 5' end side and an irrelevant sequence to the target gene, at the 3' end side. The 5' end of each of these oligonucleotide probes is phosphorylated. The oligonucleotides 133, 143 and 153 each have an irrelevant sequence to the target gene at the 5' end side and a specific sequence to the target gene, at the 3' end side. Thereafter, a ligation reaction is performed to obtain ligated oligonucleotide probes 135, 145 and 155.

The following process is performed in the same manner as shown in the first flow. More specifically, primers 161, 162, 163 and 164 are designed such that each of them corresponds to the sequence of the ligated nucleotide probe irrelevant to the target gene sequence. Using primers 161, 162, 163 and 164, the LAMP reaction is performed to obtain amplified products. In this manner, in the present invention a plurality of targets can be amplified in a single LAMP reaction, although such a multiplex reaction is difficult in conventional methods. In designing primers for use in the LAMP reaction, it is important to prevent a false-positive reaction caused by a primer dimer. Since the LAMP reaction employs four types of primers in a single reaction system, it has been difficult to design primers compared to a PCR method, TMA method, NASBA method each requiring two types of primers for amplification reaction. For this reason, it is virtually impossible to perform a LAMP reaction of a plurality of targets at the same time. In the present invention, primers are designed so as to correspond to a nucleotide sequence identical with or complementary to an irrelevant sequence to a target gene sequence. By virtue of this, the present invention can provide LAMP reaction primers commonly used no matter what type of gene is targeted. In other words, the same LAMP reaction primer can be used no matter what type of gene is targeted by just changing only the sequence portion of an oligonucleotide probe specific to that of a target gene. Since the same primers are used, it is obvious that the same reaction conditions such as reaction temperature can be used. Therefore, a plurality of amplification reactions can be easily performed at the same time.

EXAMPLES

The present invention will be explained by way of examples below. However, the present invention is not limited to these.

Example 1

1. The Primers Used in Example 1

```
Reverse transcription primer for mouse GAPDH mRNA
                                        (SEQ ID NO: 1)
5'- aactttattg atggtattca -3'

Forward inner primer
                                        (SEQ ID NO: 2)
5'- tgctgggtcg gcacagcctg aagctgacct gaaatacctg
gcctg -3'

Forward outer primer
                                        (SEQ ID NO: 3)
5'- gggtgtgtaa agctgtg -3'

Reverse inner primer
                                        (SEQ ID NO: 4)
5'-ttgttcctga tgcagtgggc agtctgcggc ggtgttctg -3'

Reverse outer primer
                                        (SEQ ID NO: 5)
5'- tgcttgtggc ctctcgtg -3'
```

2. The Oligonucleotide Probes Used in Example 1

Phosphorylated oligonucleotide probe for detecting mouse GAPDH gene (the portion of the 5' end side is a specific sequence (underlined) to the target gene and the portion of the 3' end side is an irrelevant sequence to the target gene).

```
                                        (SEQ ID NO: 6)
5'-(P) gagggccta gggagccctc tgctgggtcg gcacagcctg aatgaagaca caggccaggt atttcaggtc agccacagct ttacacaccc-3'
```

Oligonucleotide probe for detecting mouse GAPDH gene (the portion of the 5' end side is an irrelevant sequence to the target gene and the portion of the 3' end side is a specific sequence (underlined) to the target gene).

```
                                        (SEQ ID NO: 7)
5'- tgcttgtggc ctctcgtgag tctgcggcgg tgttctggtg cacctgccca ctgcatcagg aacaccaga cccccataat aacag -3'
```

3. Composition of the Reaction Solution Used in Example 1

(Numerical Value within Parentheses is a Final Concentration)
Tris-HCl pH 8.2 (20 mM), KCl (10 mM), $(NH_4)_2SO_4$ (10 mM), $MgSO_4$ (4 mM), DTT (0.5 mM), dATP (1.4 mM), dCTP (1.4 mM), dGTP (1.4 mM), dTTP (1.4 mM), TritonX-100 (0.1%), BSA (0.1 mg/mL)

4. Composition of the Enzyme Used in Example 1

Bst DNA Polymerase 8 U, Pfu-Derived Heat Resistant Ligase 2.0 U

To confirm whether a target gene can be amplified or not in accordance with the second flow of the present invention, amplified products were detected by electrophoresis. As a template, mouse glyceraldehyde-3-phosphate dehydrogenase gene (simply referred to as "GAPDH gene") was used. To perform reverse transcription of mRNA of GAPDH gene, a reverse transcription primer mentioned in Section 1 above was used as the primer 102. The reverse transcription reaction was performed in accordance with a conventional method. Then, the mRNA was decomposed by RNaseH. With the obtained cDNA, two types of oligonucleotide probes mentioned in Section 1 above were hybridized and ligated by the heat resistant ligase; at the same time, an amplification reaction was performed by using Bst DNA polymerase, the forward inner primer, the forward outer primer, the reverse inner primer and the reverse outer primer mentioned in Section 1 above.

The oligonucleotide probe 106 has the phosphorylated 5' end, a specific sequence (underlined in the sequence) to a target gene cDNA at the 5' end side and an irrelevant sequence to the target gene at the 3' end side. The oligonucleotide probe 107 has an irrelevant sequence to the target gene at the 5' end side and a specific sequence (underlined in the sequence) to a target gene cDNA at the 3' end side.

The primer 111, which is a forward inner primer, has a sequence hybridizing with a sequence portion of the oligonucleotide probe 106 irrelevant to that of the target gene, at the 3' end side, and has a sequence identical with a sequence portion of the oligonucleotide probe 106 irrelevant to that of the target gene, at the 5' end side. The primer 112, which is a forward outer primer, has a sequence hybridizing with the oligonucleotide probe 106.

The primer 111 and the primer 112 are elongated with Bst DNA polymerase, which is a DNA polymerase having strand displacement activity, to obtain the elongation product 115 of the primer 111. With the elongation product 115, the primer 121 and the primer 122 are hybridized and elongated with Bst DNA polymerase, which is a DNA polymerase having strand displacement activity. In practice, primers 111, 112, 121 and 122 were added in a reaction tube simultaneously with a reverse transcription primer. To the reaction tube, enzymes such as heat resistance DNA ligase, RNaseH and Bst DNA polymerase, a reaction substrate and a buffer solution were simultaneously supplied.

Figure 6:
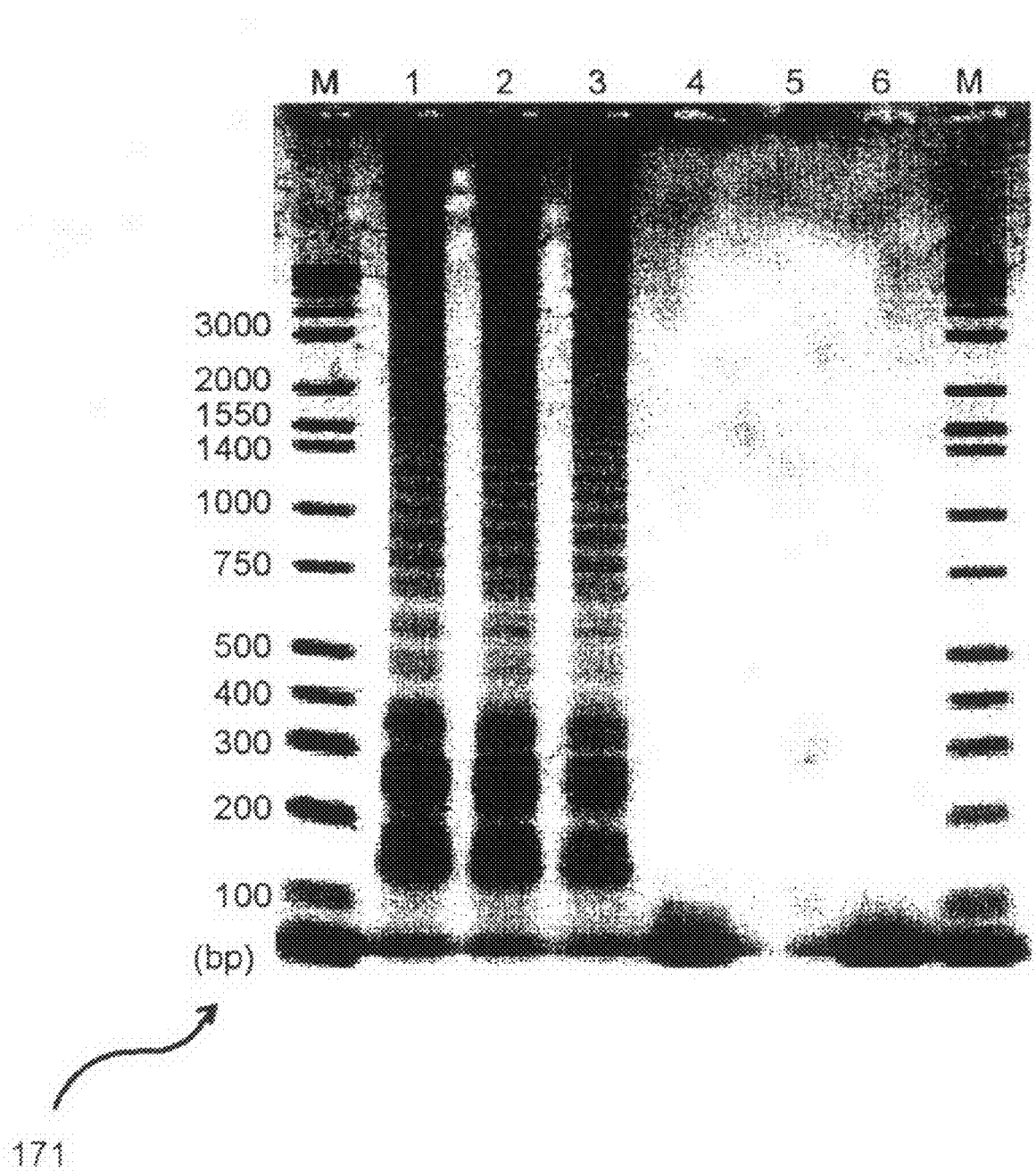
FIG. 6 shows electrophoretic analysis of amplification products obtained by the second flow of the present invention.

The composition of the amplification reaction solution and the composition of the enzymes according to the present invention are specifically mentioned in Sections 2 and 3 above. A reaction solution containing mouse mRNA serving as a template and primers was placed on a heat block set at 65° C. and incubated for 90 minutes. Thereafter, the resultant reaction product was analyzed by agarose gel electrophoresis. The electrophoretic results are shown in the electrophoresis gel image 171 of FIG. 6. A size marker was loaded to lanes represented by M at both sides and reaction products were loaded to lanes 1 to 6. Reaction products obtained from targets subjected to the reaction of the present invention consisting of reverse transcription of mouse RNA, ligation and amplification reaction were loaded in lanes 1 to 3, whereas, a negative control were loaded in lanes 4 and 5. DNA ladder of an amplified product was observed in the lanes 1 to 3, whereas no amplified product was observed in lanes 4 and 5. From the results, it is demonstrated that a desired amplification product can be obtained by the second method of the present invention. Hence, it was successfully confirmed that a gene can be amplified and detected by the present invention.

Example 2

1. The Primers Used in Example 2

(Note that: the following primers represented by SEQ ID NOS: 2 to 5 are identical with those used in Example 1).

```
Oligo dT primer for mRNA reverse transcription
                                       (SEQ ID NO: 8)
5'- tttttttttt tttttttt -3'

Forward inner primer
                                       (SEQ ID NO: 2)
5'- tgctgggtcg gcacagcctg aagctgacct gaaatacctg
gcctg -3'

Forward outer primer
                                       (SEQ ID NO: 3)
5'- gggtgtgtaa agctgtg -3'

Reverse inner primer
                                       (SEQ ID NO: 4)
5'-ttgttcctga tgcagtgggc agtctgcggc ggtgttctg -3'

Reverse outer primer
                                       (SEQ ID NO: 5)
5'- tgcttgtggc ctctcgtg -3'
```

2. The Oligonucleotide Probes Used in Example 2

Phosphorylated oligonucleotide probe for detecting human β actin gene (the portion of the 5' end side is a specific sequence (underlined) to a target gene and the portion of the 3' end side is an irrelevant sequence to the target gene).

```
                                       (SEQ ID NO: 9)
5'-(P) tcctcctgag cgcaagtatg ctgggtcggc acagcctgaa tgaagacaca ggccaggtat ttcaggtcag ccacagcttt acacaccc-3'
```

Oligonucleotide probe for detecting human β actin gene (the portion of the 5' end side is an irrelevant sequence to a target gene and the portion of the 3' end side is a specific sequence (underlined) to the target gene).

```
                                       (SEQ ID NO: 10)
5'- tgcttgtggc ctctcgtgag tctgcggcgg tgttctggtg cacctgccca ctgcatcagg aacaacaatg aagatcaaga tcattgc -3'
```

Molecular beacon for detecting human β actin gene

```
                                       (SEQ ID NO: 11)
  5'- cgacgtcaag atcattgctc ctcctgacgt cg -3'
```

Phosphorylated oligonucleotide probe for detecting human HPRT gene (the portion of the 5' end side is a specific sequence (underlined) to a target gene and the portion of the 3' end side is an irrelevant sequence to the target gene).

```
                                       (SEQ ID NO: 12)
5'-(P) gcccttgact ataatgaata ctttgctggg tcggcacagc ctgaatgaag acacaggcca ggtatttcag gtcagccaca gctttacaca ccc-3'
```

Oligonucleotide probe for detecting human HPRT gene (the portion of the 5' end side is an irrelevant sequence to a target gene and the portion of the 3' end side is a specific sequence (underlined) to the target gene).

```
                                       (SEQ ID NO: 13)
5'- tgcttgtggc ctctcgtgag tctgcggcgg tgttctggtg cacctgccca ctgcatcagg aacaacagac aagtttgttg taggatat -3'
```

Molecular beacon for detecting human HPRT gene

```
                                       (SEQ ID NO: 14)
  5'- cgacgttgta ggatatgccc ttgactatac gtcg -3'
```

3. Composition of the Reaction Solution Used in Example 2

(Numerical Value within Parentheses is a Final Concentration)

Tris-HCl pH 8.2 (20 mM), KCl (10 mM), $(NH_4)_2SO_4$ (10 mM), $MgSO_4$ (4 mM), DTT (0.5 mM), dATP (1.4 mM), dCTP (1.4 mM), dGTP (1.4 mM), dTTP (1.4 mM), TritonX-100 (0.1%), BSA (0.1 mg/mL)

4. Composition of the Enzyme Used in Example 2

Bst DNA Polymerase 8 U, Pfu-Derived Heat Resistant Ligase 2.0 U

To confirm whether a target gene can be amplified or not in accordance with the third flow of the present invention, amplified products were detected by a real-time detection system. As a template, RNA extracted from cultured cell HT29 derived from the human colon was used. The RNA extracted was subjected to reverse transcription using the reverse transcription oligo dT primer mentioned in Section 1. Subsequently mRNA is decomposed by RNaseH to prepare cDNA. More specifically, a reaction solution containing an RNA sample serving as a template and the reverse transcription primer was placed on a heat block set at 42° C. and incubated for 30 minutes.

With the cDNA thus obtained, the oligonucleotide probes (four types in total) mentioned in Section 1 were hybridized. More specifically, the oligonucleotide probes were hybridized with cDNA of β actin and cDNA of hypoxanthine phosphoribosyltransferase and ligated with the heat resistance ligase. Simultaneously with the ligation, an amplification reaction was performed using Bst DNA polymerase, the forward inner primer, forward outer primer, reverse inner primer and reverse outer primer mentioned in Section 1. As detection probes, the molecular beacon probes mentioned in Section 2 were used. The human β actin gene detection molecular beacon probe has the 5' end labeled with FAM and the 3' end labeled with BHQ1. The 1-6th base sequence and 27-32nd base sequence thereof from the 5' end are stem sequences and a 7-26th base sequence is capable of hybridizing with an amplification product. Furthermore, the human HPRT gene detection molecular beacon probe has the 5' end labeled with VIC and the 3' end labeled with BHQ1. The 1-6th base sequence and 28-34th base sequence thereof from the 5' end are stem sequences and the 7-27th base sequence is capable of hybridizing with an amplification product.

Figure 7:
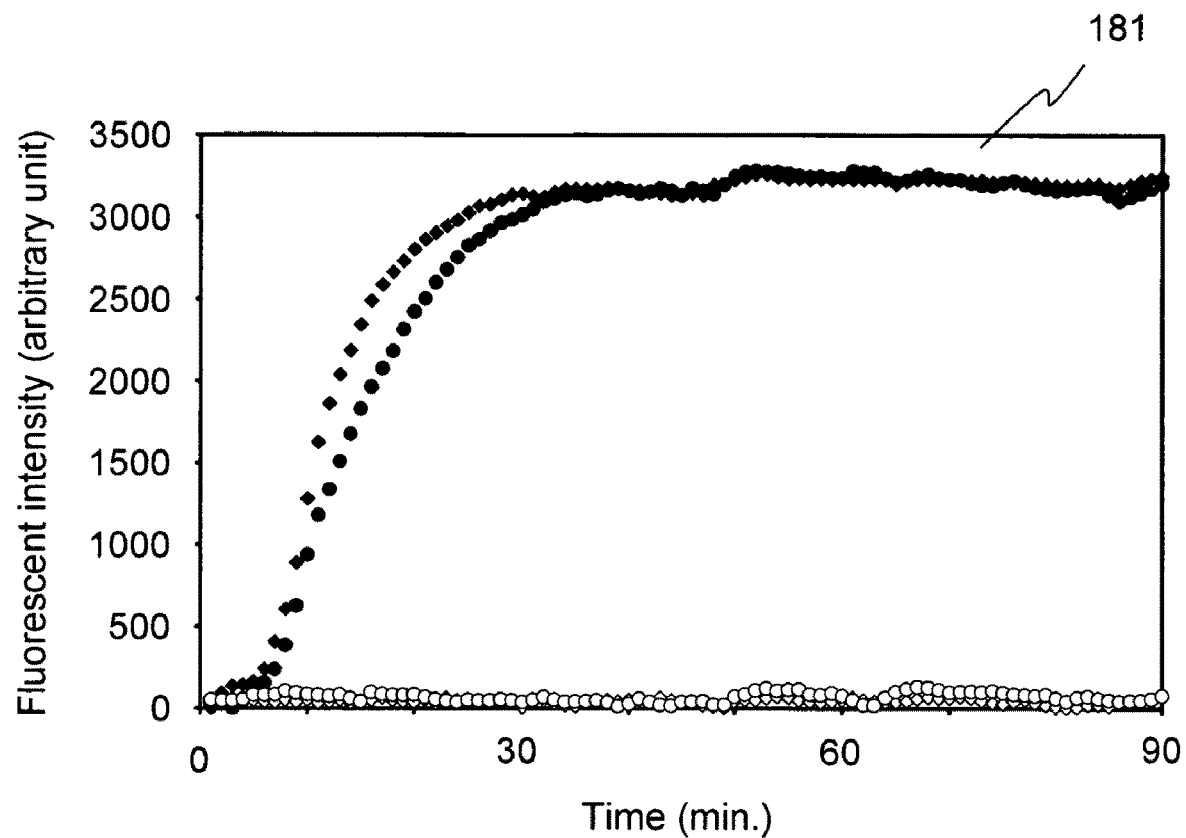
FIG. 7 is a graph showing real-time detection results of an amplified product obtained in accordance with the third flow of the present invention.

The composition of the amplification reaction solution and the composition of the enzymes are specifically mentioned in Sections 3 and 4 above. A reaction solution containing reverse transcription products obtained, 4 types of oligonucleotide probes, 4 types of amplification primers and 2 types of detection molecular beacons was placed on a real-time PCR detection system (Stratagene) set at 63° C. Fluorescent intensity of the reaction solution was measured with time for 90 minutes. The measurement results are shown in the graph 181 of FIG. 7. The transverse axis indicates time. The vertical axis indicates fluorescent intensity of FAM and VIC. The intensity of fluorescence from an amplification product was plotted. In the graph, a plot represented by a solid square shows fluorescent intensity of FAM, whereas a plot represented by a solid circle is fluorescent intensity of VIC. The fluorescent intensity values of FAM and VIC increase from about 10 minutes to 30 minutes after initiation of the reaction. The fluorescent intensity of FAM indicates that the human β actin gene is amplified. The fluorescent intensity of VIC indicates that the human HPRT gene is amplified. From this, it was demonstrated that these two genes can be amplified and detected at the same time. On the other hand, the reaction results of negative controls are indicated by fluorescent intensity of FAM represented by an open square and fluorescent intensity of VIC represented by an open circle. The fluorescent intensity curves of the negative controls containing no reverse transcription products are almost flat and do not change for the 90-minute reaction time. From this, it was demonstrated that no amplification reaction occurs in the negative controls. From these results, it was confirmed that a plurality of target RNAs can be amplified and detected in accordance with the third flow of the present invention.

According to the present invention, the presence or absence of a target nucleic acid is determined whether two types of oligonucleotide probes are ligated or not. Since amplification is performed by the LAMP method, a highly sensitive detection can be attained. Common primers can be used for LAMP amplification no matter what type of nucleic acid is targeted. In this manner, simple and highly sensitive nucleic acid amplification can be realized. In addition, a plurality of targets can be simultaneously amplified by the LAMP method using common primers. Hence, the present invention is useful in the filed of medicine including gene diagnosis and the field of life-science requiring amplification of a small amount of nucleic acid.

Free Text of Sequence Listing

SEQ ID NO: 1—description of artificial sequence: reverse transcription primer for mRNA of mouse GAPDH for use in an amplification method according to the present invention.

SEQ ID NO: 2—description of artificial sequence: forward inner primer for use in an amplification method according to the present invention.

SEQ ID NO: 3—description of artificial sequence: forward outer primer for use in an amplification method according to the present invention.

SEQ ID NO: 4—description of artificial sequence: reverse inner primer for use in an amplification method according to the present invention.

SEQ ID NO: 5—description of artificial sequence: reverse outer primer for use in an amplification method according to the present invention.

SEQ ID NO: 6—description of artificial sequence: phosphorylated oligonucleotide probe for detecting mouse GAPDH gene for use in an amplification method according to the present invention.

SEQ ID NO: 7—description of artificial sequence: oligonucleotide probe for detecting mouse GAPDH gene for use in an amplification method according to the present invention.

SEQ ID NO: 8—description of artificial sequence: oligo dT primer for use in an amplification method according to the present invention.

SEQ ID NO: 9—description of artificial sequence: phosphorylated oligonucleotide probe for detecting human β actin gene for use in an amplification method according to the present invention.

SEQ ID NO: 10—description of artificial sequence: oligonucleotide probe for detecting human β actin gene for use in an amplification method according to the present invention.

SEQ ID NO: 11—description of artificial sequence: molecular beacon for detecting human β actin gene for use in an amplification method according to the present invention.

SEQ ID NO: 12—description of artificial sequence: phosphorylated oligonucleotide probe for detecting human HPRT gene for use in an amplification method according to the present invention.

SEQ ID NO: 13—description of artificial sequence: oligonucleotide probe for detecting human HPRT gene for use in an amplification method according to the present invention.

SEQ ID NO: 14—description of artificial sequence: molecular beacon for detecting human HPRT gene for use in an amplification method according to the present invention.

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Inventor: Uematsu, Chihiro; Nakashima, Yukie;
      Hatano, Toshiyuki
<220> FEATURE:
<223> OTHER INFORMATION: Description of Artificial Sequence: designed
      reverse transcription primer which is used in the amplification
      method and hybridizes with mouse GAPDH mRNA

<400> SEQUENCE: 1
aactttattg atggtattca                                                 20
```

```
<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: designed
      forward and inner primer which is used in the amplification
      method

<400> SEQUENCE: 2
tgctgggtcg gcacagcctg aagctgacct gaaatacctg gcctg              45

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: designed
      forward and outer primer which is used in the amplification
      method

<400> SEQUENCE: 3
gggtgtgtaa agctgtg                                              17

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: designed
      reverse and inner primer which is used in the amplification
      method

<400> SEQUENCE: 4
ttgttcctga tgcagtgggc agtctgcggc ggtgttctg                      39

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: designed
      reverse and outer primer which is used in the amplification
      method

<400> SEQUENCE: 5
tgcttgtggc ctctcgtg                                             18

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence: designed
      phosphorylated oligonucleotide probe for detection of mouse GAPDH
      gene which is used in the amplification method

<400> SEQUENCE: 6
gaggggccta gggagccctc tgctgggtcg gcacagcctg aatgaagaca caggccaggt  60
atttcaggtc agccacagct ttacacaccc                                  90

<210> SEQ ID NO 7
<211> LENGTH: 85
<212> TYPE: DNA
<213> ORGANISM: Artificial Sequence
<220> FEATURE:
<223> OTHER INFORMATION: Description of Artificial Sequence: designed
``` oligonucleotide probe for detection of mouse GAPDH gene which is
used in the amplification method

<400> SEQUENCE: 7
tgcttgtggc ctctcgtgag tctgcggcgg tgttctggtg cacctgccca ctgcatcagg    60
aacaaccaga cccccataat aacag    85

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: designed
      oligo dT primer which is used in the amplification method

<400> SEQUENCE: 8
tttttttttt tttttttt    18

<210> SEQ ID NO 9
<211> LENGTH: 88
<212> TYPE: DNA
<213> ORGANISM: Artificial Sequence
<220> FEATURE:
<223> OTHER INFORMATION: Description of Artificial Sequence: designed
      phosphorylated oligonucleotide probe for detection of human
      beta-actin gene which is used in the amplification method

<400> SEQUENCE: 9
tcctcctgag cgcaagtatg ctgggtcggc acagcctgaa tgaagacaca ggccaggtat    60
ttcaggtcag ccacagcttt acacaccc    88

<210> SEQ ID NO 10
<211> LENGTH: 87
<212> TYPE: DNA
<213> ORGANISM: Artificial Sequence
<220> FEATURE:
<223> OTHER INFORMATION: Description of Artificial Sequence: designed
      oligonucleotide probe for detection of human beta-actin gene
      which is used in the amplification method

<400> SEQUENCE: 10
tgcttgtggc ctctcgtgag tctgcggcgg tgttctggtg cacctgccca ctgcatcagg    60
aacaacaatg aagatcaaga tcattgc    87

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: designed
      molecular beacon probe for detection of human beta-actin gene
      which is used in the amplification method

<400> SEQUENCE: 11
cgacgtcaag atcattgctc ctcctgacgt cg    32

<210> SEQ ID NO 12
<211> LENGTH: 93
<212> TYPE: DNA
<213> ORGANISM: Artificial Sequence
<220> FEATURE:
<223> OTHER INFORMATION: Description of Artificial Sequence: designed
      phosphorylated oligonucleotide probe for detection of human HPRT
      which is used in the amplification method

<400> SEQUENCE: 12

-continued

```
gcccttgact ataatgaata ctttgctggg tcggcacagc ctgaatgaag acacaggcca      60
ggtatttcag gtcagccaca gctttacaca ccc                                  93

<210> SEQ ID NO 13
<211> LENGTH: 88
<212> TYPE: DNA
<213> ORGANISM: Artificial Sequence
<220> FEATURE:
<223> OTHER INFORMATION: Description of Artificial Sequence: designed
      oligonucleotide probe for detection of human HPRT gene which is
      used in the amplification method

<400> SEQUENCE: 13
tgcttgtggc ctctcgtgag tctgcggcgg tgttctggtg cacctgccca ctgcatcagg      60
aacaacagac aagtttgttg taggatat                                        88

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: designed
      molecular beacon probe for detection of human HPRT gene which is
      used in the amplification method

<400> SEQUENCE: 14
cgacgttgta ggatatgccc ttgactatac gtcg                                 34
```

What is claimed is:

1. A method for amplifying a nucleic acid comprising:

hybridizing a first probe and a second probe with a target nucleic acid, said first probe having a first sequence complementary to the target nucleic acid at the 3' end of the first probe and the first probe having a second sequence noncomplementary to the target nucleic acid at the 5' end of the first probe, and the second probe, having a third sequence noncomplementary to the target nucleic acid at the 3' end of the second probe and a fourth sequence complementary to the target nucleic acid at the 5' end of the second probe, said 5' end of the second probe being phosphorylated;

subsequently forming a ligated template by ligating the 3' end of the first probe to the 5' end of the second probe by a ligation reaction; and amplifying the ligated template by repeating the following steps (a) to (g):

(a) hybridizing a first primer, with the ligated template, wherein the first primer has a fifth sequence identical to a first region of the third sequence of the ligated template, at one end of the first primer, and the first primer has a sixth sequence complementary to a second region of the third sequence of the ligated template at the other end of the first primer, the first region on the ligated template being located to the 5' side of the second region of the ligated template; and elongating the first primer, thereby obtaining a first amplification template;

(b) hybridizing a second primer, with the ligated template, wherein the second primer has a seventh sequence complementary to a third region of the third sequence of the ligated template, the third region located on the 3' side of the second region of the ligated template, and elongating the second primer with DNA polymerase having strand displacement activity, thereby dissociating the first amplification template from the ligated template to form a first dissociated amplification template, wherein a first loop structure can be formed by hybridizing the fifth sequence of the first dissociated amplification template with a sequence of the first dissociated amplification template, complementary to the first region of the ligated template and produced during the elongating in step (a);

(c) hybridizing a third primer, with the first dissociated amplification template, wherein the third primer has an eighth sequence of the third primer which is complementary to a first region of the first dissociated amplification template, the first region being produced from the second sequence of the first probe during the elongation of step (a), and wherein the third primer has a ninth sequence identical to a second region of the first dissociated amplification template, the second region being produced from the second sequence of the first probe during the elongating in step (a), the second region being at the 3' side of the first region and elongating the third primer, thereby obtaining a second amplification template;

(d) hybridizing a fourth primer, with the first dissociated amplification template, wherein the fourth primer has a tenth sequence, complementary to a third region of the first dissociated amplification template, the third region being produced from the first probe during the elongating of step (a), the third region of the first dissociated amplification template being on the 5' side of the second region of the first dissociated amplification template, and elongating the fourth primer by DNA polymerase having strand displacement activity; thereby dissociating the second amplification template from the first dissociated amplification template to form the second dissociated amplification template, wherein a second loop structure can be formed by hybridizing the ninth sequence of the second dissociated amplification template with a sequence of the second dissociated amplification template complementary to the second region of the first dissociated amplification template, produced during the elongating of step (c);

(e) synthesizing a complementary strand from the 3' end of the second dissociated amplification template;

(f) hybridizing a fifth primer, with the second dissociated amplification template having an amplification formed on the 3' end by hybridizing at least a part of the fifth sequence at the 5' end and at least a part of the sixth sequence at the 3' end, and elongating the fifth primer using DNA polymerase having strand displacement activity to displace the complementary strand synthesized in the step (e), thereby rendering the 3' end of the strand displaced to be capable of forming base pairing; and (g) forming a new template from the strand whose 3' end is rendered to be capable of forming base pairing in the step (f) as a new template to be used in the step (e).

2. The method for amplifying a nucleic acid according to claim 1, further comprising:

(h) synthesizing a complementary strand from the 3' end of the new template;

(i) hybridizing a sixth primer, with the new template, the new template having a loop formed at the 3' end, the sixth primer having at least a part of the eighth sequence at the 5' end of the sixth primer and at least a part of the ninth sequence at the 3' end of the sixth primer, elongating the sixth primer with DNA polymerase having strand displacement activity to displace the complementary strand synthesized in the step (h), thereby rendering the 3' end of the strand displaced to be capable of forming base pairing; and (j) forming a new template from the strand whose 3' end is rendered to be capable of forming base pairing in the step (i) as the new template to be used in the step (e).

3. The method for amplifying a nucleic acid according to claim 1, wherein the fifth primer is identical to the first primer.

4. The method for amplifying a nucleic acid according to claim 2, wherein that the sixth primer is identical to the third primer.

5. The method for amplifying a nucleic acid according to claim 1, wherein, in the step (f) a seventh primer having a complementary sequence to at least one part of the eighth sequence is hybridized with a loop formed at the 5' end side of the second dissociated amplification template and elongated with DNA polymerase having strand displacement activity.

6. The method for amplifying a nucleic acid according to claim 2, wherein, in the step (i), an eighth primer having a sequence complementary to at least a part of the fifth sequence with a loop formed at the 5' end side of the new template and elongated with DNA polymerase having strand displacement activity.

7. The method for amplifying a nucleic acid according to claim 1, wherein the 3' end of the third sequence of the second probe is modified with phosphorylation or amination.

8. The method for amplifying a nucleic acid according to claim 1, wherein a plurality of types of target nucleic acids are simultaneously amplified and detected in a single reaction tube by hybridizing the two types of oligonucleotide probes with each of the target nucleic acids, ligating them by a ligation reaction, and allowing the first, second, third and fourth primers to act on each of the ligated oligonucleotide probes.

* * * * *